United States Patent [19]

Wilharm et al.

[11] Patent Number: 5,395,914
[45] Date of Patent: Mar. 7, 1995

[54] POLYARYLENE ETHERS CONTAINING XANTHONE UNITS, A PROCESS FOR THEIR PREPARATION, AND THEIR USE

[75] Inventors: Peter Wilharm, Gersthofen; Thomas Weller, Mainz; Michael Meier, Frankfurt am Main, all of Germany

[73] Assignee: Hoechst Aktiengesellschaft, Frankfurt am Main, Germany

[21] Appl. No.: 67,709

[22] Filed: May 26, 1993

[30] Foreign Application Priority Data

May 26, 1992 [DE] Germany .................. 42 17 347.7

[51] Int. Cl.$^6$ ................ C08G 8/02; C08G 14/00
[52] U.S. Cl. .................... 528/125; 528/126; 528/128; 528/174; 528/220
[58] Field of Search ........ 528/125, 126, 174, 128, 528/220

[56] References Cited

U.S. PATENT DOCUMENTS

| | | | |
|---|---|---|---|
| 3,546,167 | 12/1970 | Darms | 528/125 |
| 3,763,103 | 10/1973 | Newton et al. | 528/125 |
| 3,985,783 | 10/1976 | Johnson et al. | 558/376 |

FOREIGN PATENT DOCUMENTS

| | | |
|---|---|---|
| 0001879 | 5/1979 | European Pat. Off. . |
| 0182648 | 5/1986 | European Pat. Off. . |
| 0193187 | 9/1986 | European Pat. Off. . |
| 60-071635 | 4/1985 | Japan . |
| 1238124 | 7/1971 | United Kingdom . |

OTHER PUBLICATIONS

Derwent Abstract, AN 85-132632 of JP 60 071 636 (Sep. 20, 1985).
Derwent Abstract, AN 85-132631 of JP 60 071 635 (Apr. 23, 1986).
Chemical Abstracts, vol. 77, No. 27, "Reactions induced by pyridine hydrochloride", p. 389 (1972).
Derwent Abstract, AN 88-202963 of JP 63 141 942 (Jun. 14, 1988).

*Primary Examiner*—John Kight, III
*Assistant Examiner*—P. Hampton-Hightower
*Attorney, Agent, or Firm*—Connolly & Hutz

[57] ABSTRACT

Polyarylene ethers that contain xanthone units and have a very high heat resistance can be prepared from inexpensive, readily accessible monomers by polycondensation in a basic medium under essentially anhydrous conditions in the presence or absence of an aromatic solvent at temperatures of from 150° to 400° C. Xanthone monomers and also hydroxyhalogen-substituted benzophenone compounds may be used as starting materials.

18 Claims, No Drawings

POLYARYLENE ETHERS CONTAINING XANTHONE UNITS, A PROCESS FOR THEIR PREPARATION, AND THEIR USE

The present invention relates to polyarylene ethers containing xanthone units, to a process for their preparation from inexpensive starting materials, and to their use in the production of moldings.

Polyarylene ethers have been known for a long time and are notable for their valuable practical properties, such as high heat resistance and good electrical and mechanical properties. The partly crystalline polyarylene ether ketones in particular are also extremely resistant to solvents and chemical attack.

AB monomers, i.e. self-condensable monomers, have been used at various times to prepare polyarylene ether ketones. Such monomers have the disadvantage that the attainment of high molecular weights does not depend on the maintenance of an exact stoichiometry, as in the reaction of AA monomers with BB monomers, for example in the reaction of bisphenols with activated dihalogen aromatics.

The nucleophilic process is generally advantageously used to prepare polyarylene ether ketones having a high molecular weight, since polymers that are more structurally uniform can be obtained in this way than by the electrophilic process.

It is known that hydroxyhalogen aromatics (AB monomers) that are at least binuclear and whose chlorine or fluorine leaving groups are activated by electron-withdrawing groups in the ortho-position or para-position can react under conditions of nucleophilic polycondensation to form polyarylene ether ketones. For example, the corresponding polyarylene ether ketone is obtained by a copper-catalyzed nucleophilic polycondensation of 4-chloro-4'-hydroxybenzophenone (EP-B 0 182 648). This route is attractive in that the chlorine monomers used are inexpensive and easy to prepare. However, the disadvantage is that the chlorine monomers used in the process are relatively unreactive compared to the corresponding fluorine monomers, and in general require the use of copper compounds as catalysts. These copper catalysts can be completely removed only with difficulty, if at all, from the resultant polyarylene ether ketones and considerably impair the melt stability. Furthermore, the copper-containing effluent formed in the working-up has to be purified for environmental protection reasons, which is a complicated and expensive procedure.

Furthermore, heterocyclic AB monomers are known that can react under the conditions of nucleophilic polycondensation (DE-C 20 38 240). This patent describes the polycondensation of 2-hydroxy-6-chlorodibenzooxathiine. Although these polymers are very heat resistant and have high glass transition temperatures, they have a high water absorption and low resistance to solvents.

It is also known that polyarylene ether ketones having xanthone units can be prepared from corresponding polymeric chlorohydroxybenzophenones (DE-C 18 06 419). The disadvantage is that the polyketones used as starting materials are difficult to prepare and, as our own experiments have demonstrated, the resultant polymers are not melt-processible.

Furthermore, a process is described for preparing linear, high molecular weight, thermoplastic polyether ketones in which, inter alia, also xanthone monomers of the AA type are reacted with bisphenols of the BB type (GB-B 1 238 124). However, in general polymers such as are described in the present invention cannot be prepared. Moreover, it is a disadvantage that the stoichiometry has to be observed extremely accurately in order to obtain products having a high molecular weight.

Polymers with recurring units of the formula

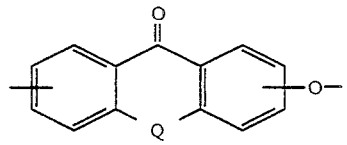

are also known, where

Q is —C(R$^1$)$_2$—, —CO—, —O—, —S—, —NR$_2$—, —Si(R$^3$)$_2$—, —P(O)R$^4$—, where R$^1$ is hydrogen, alkyl groups having 1 to 5 carbon atoms or phenyl groups, and R$^2$, R$^3$ and R$^4$ are alkyl groups having 1 to 5 carbon atoms or phenyl groups (JP-A 60-71635). These polymers are obtained by self-condensation of the corresponding hydroxyhalogen monomers. A xanthone monomer, namely 3-fluoro-7-hydroxyxanthen-5-one is also mentioned in the list of suitable phenols, though this compound, as our own experiments have shown, cannot react under the experimental conditions mentioned in the examples to form the corresponding aromatic polyether.

It is an object of the present invention to provide linear polyarylene ethers having very high heat resistance from inexpensive, easily accessible monomers.

The present invention thus relates to polyarylene ethers with the recurring units of the formulae

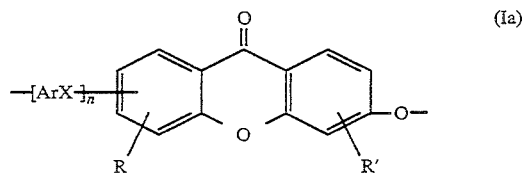  (Ia)

and/or

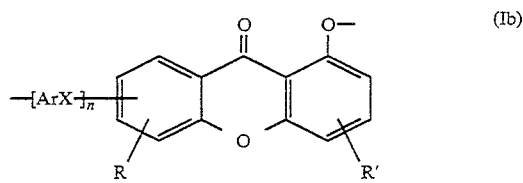  (Ib)

where R and R' which are the same or different, are hydrogen, alkyl, alkoxy, aryl, aryloxy groups, benzofused radicals, preferably hydrogen, methyl, phenyl, methoxy, phenoxy groups, but in particular hydrogen, Ar is a divalent aromatic radical, preferably a phenylene group, X is a direct bond, —O—or —S—, and n is zero or one.

The preparation of polymers and copolymers having recurring units of the formula (Ia) or (Ib) comprises (a) the nucleophilic polycondensation under essentially anhydrous conditions in the presence or absence of a polar, aprotic aromatic solvent (i) of at least one hydroxyhalogen-substituted xanthone of the formula (IIa) or (IIb)

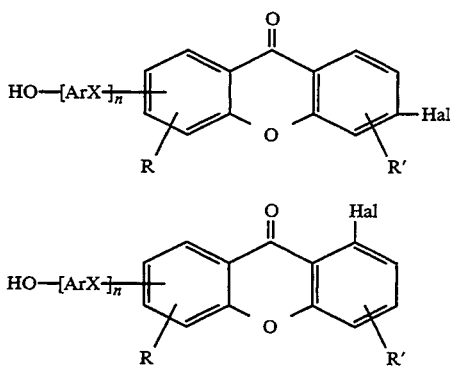

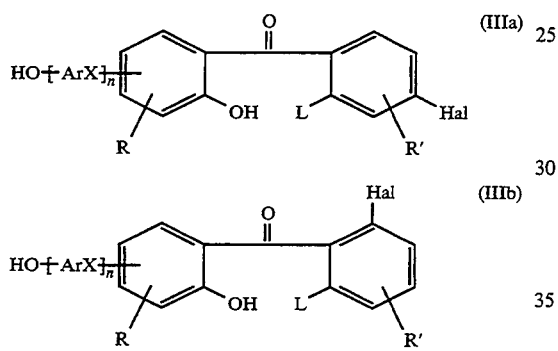

where
R, R', Ar X and n have the above meanings, and
Hal is chlorine or fluorine groups, in particular chlorine groups, or (ii) of at least one hydroxyhalogen-substituted benzophenone compound of the formula (IIIa) or (IIIb)

where
R, R', Ar X Hal and n have the above meanings and,
L is a fugic group that can be displaced by intramolecular nucleophilic substitution, preferably a chlorine or fluorine group, in particular a chlorine group, or (b) the nucleophilic polycondensation under basic conditions of at least one hydroxyhalogen compound according to (a) together with at least one hydroxyhalogen compound of the formula (IV)

HO—Ar'—Hal     (IV)

where Ar' is a divalent aromatic radical having 12 to 26, preferably 12 to 20, carbon atoms, which contains at least one keto or sulfonyl group that is in the ortho-position or para-position to the Hal group, and Hal is a chlorine or fluorine group that is situated in the outermost aromatic nucleus.

Some of the xanthone compounds according to formula (Ia) or (Ib) are known or can be prepared by known processes. For example benzophenone compounds according to formula (IIIa) or (IIIb) can be used as starting compounds for their preparation, for example by intramolecular substitution (Chem. Pharm. Bull. 38, 1266 (1990)).

Furthermore, xanthone compounds according to formula (IIa) or (IIb) can be prepared by electrophilic cyclization (Comprehensive Heterocyclic Chemistry, Vol. 3, p. 647 ff and p. 737 ff, Pergamon Press (1984), and also R. C. Elderfield, Ed., Heterocyclic Chemistry, Vol. II, p. 419 ff, Wiley (1951)).

Suitable xanthone compounds according to formula (IIa) or (IIb) are for example

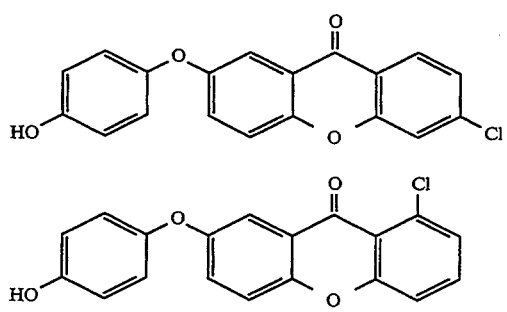

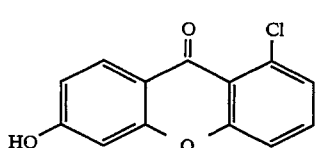

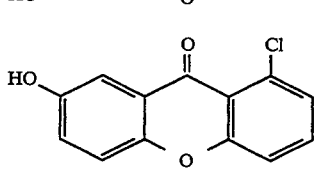

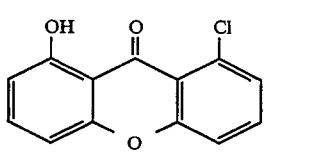

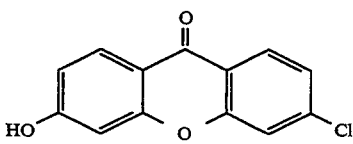

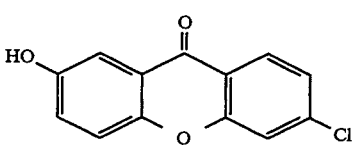

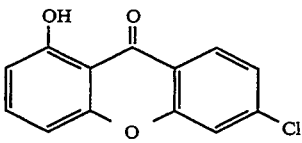

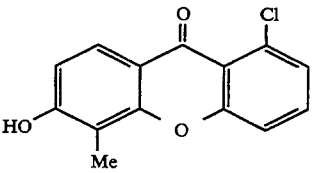

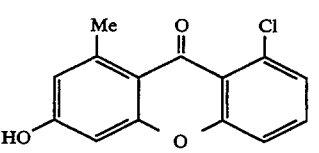

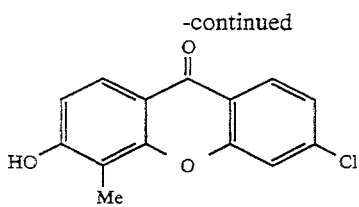
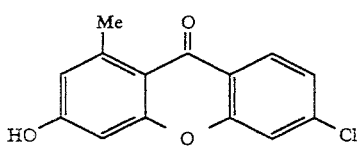
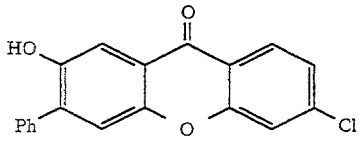
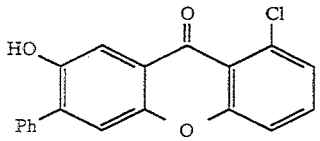
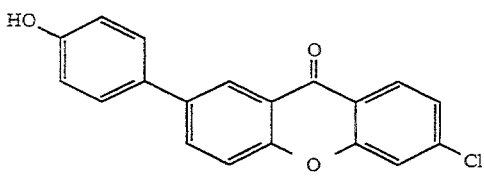
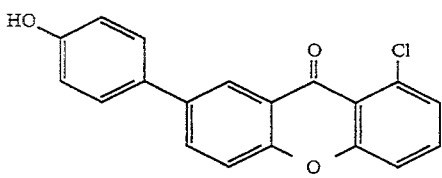

and the corresponding nuclear-fluorinated compounds. In the formulae Me is a methyl group and Ph is a phenyl group. The hydroxyhalogen-substituted benzophenone compounds of the formula (IIIa) or (IIIb) may be obtained in a known manner, for example by Fries rearrangement of the correspondingly substituted aromatic esters or by acylation of the corresponding phenols or phenol methyl ethers.

Suitable benzophenone compounds according to formula (IIIa) or (IIIb) are for example

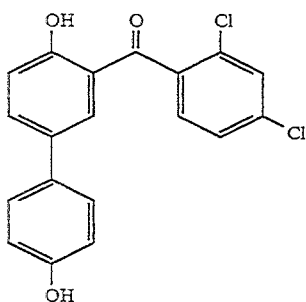

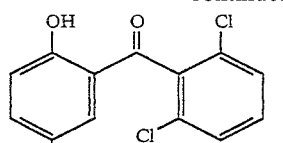
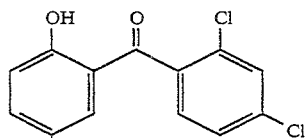
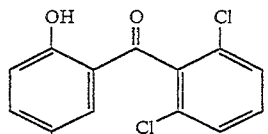
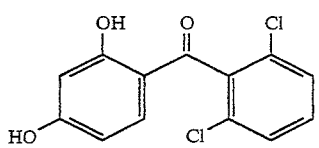
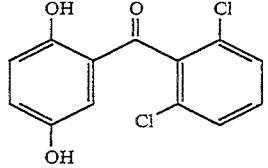
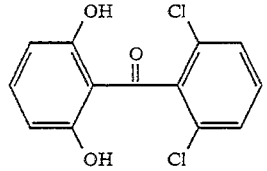
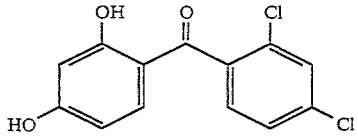

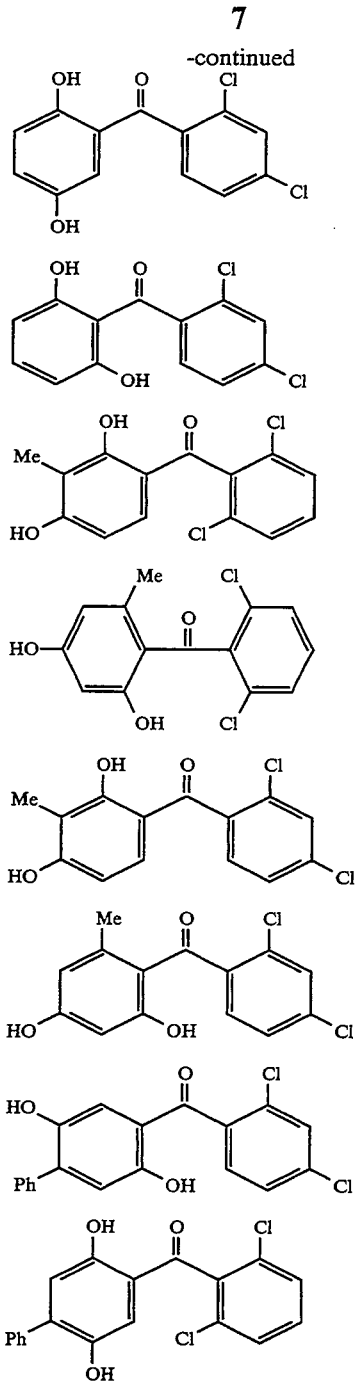

-continued and the corresponding nuclear-fluorinated compounds, Me and Ph being as defined above. Compounds according to (IIa), (IIb), (IIIa) or (IIIb) or mixtures thereof can be used to prepare polyarylene ethers that contain recurring units of the formula (Ia) or (Ib).

Moreover, monohydroxymonohalogen compounds according to formula (IV) may be used for the preparation of copolymers. Examples of such comonomers are compounds according to formulae (V) or (VI)

HO—Ph—T—Ph'—Hal     (V),

HO—Ph—Y—Ar'—Z—Ph'—Hal     (VI)

where Ph and Ph', which are the same or different, are an unsubstituted phenylene group or a phenylene group substituted with methyl or phenyl groups, Ar' as a divalent radical is a phenylene or biphenyl group, T is a keto or sulfone group, Y is a direct bond or an ether, keto or sulfone group, Z is a keto or sulfone group and Hal is halogen, preferably chlorine or fluorine, which in each case is in the ortho-position or para-position relative to Z.

Monohydroxymonohalogen compounds that may be used include for example 4-chloro-4'-hydroxybenzophenone, 4-(4'-chlorobenzoyl)-4'-hydroxybiphenyl, 4-(4'-chlorobenzoyl)-4'-hydroxydiphenyl ether, 4-chloro-4'-hydroxyterephthalophenone, 4-chloro-4'-hydroxyisophthalophenone, 4-(4'-hydroxybenzoyl)-4'-(4-chlorobenzoyl)biphenyl, 4-chloro-4'-hydroxydiphenyl sulfone, 4-hydroxy-4'-(4'-chlorophenylsulfonyl)-biphenyl, 4-(4-hydroxyphenylsulfonyl)-4'-(4-chlorophenylsulfonyl)biphenyl, 4-hydroxy-4'-(4'-chlorophenylsulfonyl)diphenyl ether, 4-hydroxy-3,5-dimethyl-4'-chlorobenzophenone, 4-hydroxy-3,5-di-phenyl-4'-chlorobenzophenone, the corresponding fluorine-substituted compounds, or mixtures of the above compounds.

Preference is given to 4-chloro-4'-hydroxybenzophenone, 4-chloro-4'-hydroxyterephthalophenone, 4-chloro-4'-hydroxyisophthalophenone, 4-chloro-4'-hydroxydiphenylsulfone, 4-hydroxy-3,5-dimethyl-4'-chlorobenzophenone, their fluorine analogs, and mixtures thereof.

The preparation of the polymers according to the invention by nucleophilic polycondensation is performed in a manner known per se under conditions—process conditions, solvents and additives—that have become known in the preparation of other polyarylene ethers (EP 0 001 879, EP 0 193 187, U.S. Pat. Nos. 4,108,837, 4,175,175 and in "Comprehensive Polymer Science", Vol. 5, p. 483 ff. and p. 561 ff., Ed. G. Allen, Pergamon Press 1989 and in Polymer 22, 1096 (1981)).

A particular advantage of the process according to the invention is that in general chlorine monomers instead of the more expensive fluorine monomers can be used. The reactivity in the nucleophilic substitution of chlorine groups in the ortho-position or para-position relative to the keto group in the xanthone monomers is considerably increased compared to the corresponding chlorobenzophenone monomers.

Preference is given to an embodiment of the process in which xanthone compounds (IIa) or (IIb) are produced in situ from benzophenone compounds according to formula (IIIa) or (IIIb) in a stage preceding the polycondensation. An advantage is that the prior isolation of the xanthones is not necessary.

The azeotropic process is suitable for the in situ preparation of the xanthone compounds. The water formed in the phenolate synthesis is continuously removed form the reaction mixture by means of an azeotrope former.

Suitable water-azeotrope formers are all substances that boil at atmospheric pressure in the region of the reaction temperature and that are miscible with the reaction mixture without undergoing chemical reactions. Such azeotrope formers are for example: chlorobenzene, toluene, xylene, long-chain aliphatic hydrocarbons, cyclohexane.

If diphenylsulfone, xanthone, benzophenone or mixtures thereof are used as polycondensation solvents, an embodiment of the process is preferred in which the in situ preparation of the xanthone compounds and the polycondensation take place under successive stepwise increases in the reaction temperature without the addition of an azeotrope former.

The polycondensation is carried out in the presence of an inorganic base. Suitable compounds according to the invention are alkali metal hydroxides, alkali metal carbonates, alkali metal bicarbonates and alkali metal fluorides. Preference is given to the carbonates and bicarbonates of sodium and potassium, such as sodium carbonate, sodium bicarbonate, potassium carbonate, potassium bicarbonate, and mixtures thereof.

The total amount of base is generally calculated so that at least one mole of metal atoms, preferably 1.0 to 1.2 moles of metal atoms, are present per mole of hydroxyl groups.

If an alkali metal hydroxide is used as base, this is preferably reacted with the phenolic OH groups of the monomers according to formula (IIa), (IIb), (IIIa) or (IIIb), in a stage preceding the polycondensation, to form the relevant alkali metal phenolates. The isolated phenolates should have a grain size of less than 0.5 mm, preferably 1 to 350 μm.

The phenolate formation when using alkali metal hydroxides should take place at low temperatures, preferably at a temperature of less than 100° C., in order to avoid a hydrolysis of the halogen groups. For example, the alkali metal phenolates are expediently obtained from water-alcohol mixtures with the addition of stoichiometric amounts of alkali metal hydroxide followed by removal of the solvent at temperatures of less than 100° C.

The preparation of the polymers according to the invention is performed either in a polar, aprotic solvent or in the absence of a solvent in the melt. Suitable solvents for carrying out the polycondensation are for example aromatic sulfoxides and sulfones, diphenyl sulfone, ditolyl sulfone, dibenzothiophene S,S-dioxide, 4-phenylsulfonylbiphenyl and cyclic ureas, such as 1,3-dimethyl-3,4,5,6-tetrahydro-2-pyrimidone, aromatic ketones such as xanthone, thioxanthone, benzophenone, fluorenone, 4-phenoxybenzophenone and isophthalophenone.

Particularly preferred are diphenyl sulfone, xanthone, benzophenone and mixtures thereof.

When using aromatic sulfones as solvents the bases are employed in ground and dried form, the grain size being less than 0.4 mm, preferably from 1 to 350 μm.

The polar, aprotic solvents are used in such amounts that the reaction solutions have a solids content of from 5 to 50% by weight, preferably from 20 to 45% by weight.

In order to achieve high molecular weights it is important to ensure essentially anhydrous conditions in the reaction mixture during the polycondensation reaction. Water formed during the polycondensation reaction should therefore immediately be removed from the system in order to avoid a hydrolysis of the preferably chlorine-containing monomers. This can be achieved using an azeotrope former, applying a subatmospheric pressure, or preferably by passing a stream of nitrogen through or over the reaction mixture, followed by distillation.

The lower limit of the reaction temperature is determined by the melting point of at least one of the components or of the solvent, and the upper limit is determined by the decomposition temperature of the condensation partners, of the solvent, or of the resultant polymers.

The reaction temperature employed depends, inter alia, on the reactivity of the monomers and of the solvent and is generally in the range from 150° to 400° C. preferably from 200° to 350° C.

The polycondensation is preferably carried out in an inert gas atmosphere, for example under a nitrogen or argon atmosphere.

One way of adjusting the desired molecular weight is to add a chain-terminating compound (regulator) in the polycondensation. Suitable chain terminators are for example methyl chloride, 4-chlorodiphenyl sulfone, 4-fluorobenzophenone, 4,4'-difluorobenzophenone and 1,4-bis(4-fluorobenzoyl)benzene.

The aforementioned compounds serve at the same time to stabilize any free phenolate terminal groups that may be present.

The reaction solution can be worked up according to the conventional processes that are known per se. A finely particulate material is advantageously obtained from the melt, which is freed from polycondensation solvents (e.g. xanthone) by extraction with a suitable solvent (e.g. acetone, methanol or toluene). Also, a quenched reaction solution that has been obtained as a solid in the form of a thin layer by for example pouring the solution onto a cold metal plate may, after having been finely ground, be used for the extraction. The residues of inorganic salts may then be removed by extraction with water and if necessary dilute acid.

The polymers prepared according to the present process have an inherent viscosity of at least 0.2 dl/g, preferably from 0.2 to 2.5 dl/g, in particular from 0.4 to 1.8 dl/g.

The polyarylene ethers prepared by the above process are notable for high heat resistance and may advantageously be used to produce moldings such as fibers, films, injection-molded parts, adhesives and coating agents, and also as matrix material for composites and cable sheathings. The polyarylene ethers are particularly suitable for applications in which a high thermal stress and/or an oxidizing atmosphere have to be taken into account.

The polyarylene ethers can furthermore be mixed and processed with other polymers and can also be mixed with fillers, such as glass fibers, carbon fibers, aramid fibers, mineral fillers and reinforcing materials such as calcium carbonate, talcum, magnesium carbonate, mica and conventional additives such as stabilizers, pigments and mold release agents.

The inherent viscosities (I.V.) specified in the following examples are mean values and were determined by the method of Sorenson et al., described in "Preparative Methods of Polymer Chemistry", Interscience (1968), p. 49: 0.125 g of polymer in 25 ml of sulfuric acid (d=1.84 g/cm$^3$) at 25° C.

EXAMPLES

Preparation of the monomers:

1) 2',4'-Dichloro-2,5-dihydroxybenzophenone: 190 g of 1,4-dimethoxybenzene, 138 g of 2,4-dichlorobenzoyl chloride and 2000 ml of 1,2-dichlorobenzene were cooled to 15° C. while stirring in a 4 liter capacity flask equipped with mechanical stirrer, reflux condenser with attached bubble counter, thermostatically controlled heating bath, and internal thermometer. 485 g of anhydrous aluminum trichloride were then added in portions in such a way that the internal temperature remained below 40° C. After all the aluminum trichloride had been metered in, the contents were heated slowly to 80° C. the colour of the reaction mixture changing to light yellow and the viscosity strongly increasing. The reaction mixture was then stirred until the evolution of gas noticeably decreased.

The reaction mixture was added to a mixture of 1 kg of ice, 2,1 of water and 500 ml of 30% strength hydrochloric acid and stirred vigorously for 2 hours. The precipitated product is suction filtered, washed with water, and dried at 60° C.

Yield 60% (yellow crystals), melting point 156° C.

2) 2-Hydroxy-6-chloroxanthone: 27 g of 2',4'-dichloro-2,5-dihydroxybenzophenone, 10.5 g of sodium carbonate and 100 ml of N-methylpyrrolidone were heated for 2 hours at 160° C. while stirring, an intensely yellow solution being formed under a strong evolution of carbon dioxide. The reaction mixture was worked up by allowing it to cool to 80° C. and then adding 100 ml of water dropwise while stirring. The precipitated crystal mass was suction filtered and dried at 50° C. under reduced pressure. Yield 80%, (colorless crystals), melting point 268° C.

The following compounds were obtained by similar reactions: 2',4'-dichloro-2,4-dihydroxybenzophenone, melting point 159° C.; 3-hydroxy-6-chloroxanthone, melting point 331° C.; 2',4'-dichloro-2-hydroxy-5- (4-hydroxyphenyl) benzophenone and 3-chloro-7-(4-hydroxyphenyl)xanthone.

3) Polycondensation: The polycondensation was carried out in the following apparatus:

2 liter capacity double-jacket stirred vessel of V4A steel (heated with heat transfer oil), equipped with bottom drainage valve, inlet for nitrogen shielding gas, stirrer of V4A steel, thermosensor for measuring the internal temperature, waste gas tube dipping into water (bubble counter).

The viscosity of the reaction solution was measured by measuring the torque on the stirrer shaft.

A constant stream of nitrogen was passed over the reaction mixture throughout the course of the reaction in order to remove the water formed in the reaction.

The following compounds were added to the stirred vessel: 265 g of 2-hydroxy-6-chloroxanthone, 58 g of sodium carbonate (dried and ground), 8.4 g of sodium bicarbonate, 5 g of potassium fluoride (spray-dried), 600 g of diphenyl sulfone and 500 g of xanthone. The vessel contents were first of all heated to 200° C. After 30 minutes at 200° C. the temperature was raised to 320° C. over the course of 1 hour. The color of the reaction solution changes from the initial orange to gray with increasing viscosity. 5 g of 1,4-bis(4-fluorobenzoyl)benzene were then added as chain terminator and the solution was stirred for a further 30 minutes.

The viscous reaction solution was poured onto a metal plate, the thin layer obtained after cooling was ground and the polymer was isolated therefrom as follows: 200 g of reaction mixture were extracted in each case for 1 hour: once with 1.5 l of acetone at 25° C., twice with 1.5 l of acetone at the reflux temperature, three times with 1.5 l of water at 80° C., once with 1.5 l of acetone at the reflux temperature.

The reaction product was then dried to constant weight at 120° C. under reduced pressure. Yield 83%. The polymer had a melting point of 460° C. according to DSC measurements, and the inherent viscosity was 0.81 dl/g.

4) Experimental apparatus: 250 ml three-necked flask equipped with heating mantle, inlet for nitrogen shielding gas, glass stirrer, internal thermometer, waste gas tube dipping into water (bubble counter). The viscosity of the reaction solution was measured by measuring the torque on the stirrer shaft.

A constant stream of nitrogen was passed over the reaction mixture throughout the course of the reaction in order to remove the water formed in the reaction.

The following compounds were added to the reaction vessel: 13.23 g of 2,5-dihydroxy-2',4-dichlorobenzophenone, 5.82 g of sodium carbonate (dried and ground), 0.55 g of potassium bicarbonate, 1 g of potassium fluoride (spray-dried), 120 g of diphenyl sulfone/xanthone (1:1). The mixture was heated for 1 hour at 200° C. while stirring, the temperature was raised to 320° C. in the course of 1 hour, and the reaction mixture was stirred for a further 3 hours at this temperature. 0.5 g of 4,4'-dichlorodiphenyl sulfone was then added as chain terminator and the solution was stirred for a further 20 minutes. The reaction solution is worked up in a similar manner to Example 1, the polymer obtained having the same properties as in Example 1.

5 to 7). Further examples are given in the following table, which were carried out in a similar manner to Examples 3 and 4.

Additional polymer examples

| Example | Monomer | Reaction conditions | Polymer properties |
|---|---|---|---|
| 5 | 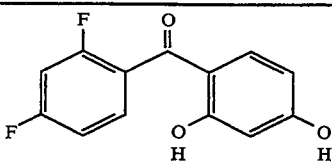 | Example 3<br>Base: K$_2$CO$_3$<br>Solvent:<br>xanthone | I.V. = 0.41<br>No melting<br>below 400° C. |
| 6 | 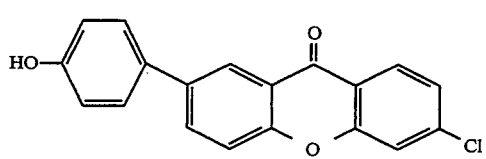 | Example 4<br>Base: Na$_2$CO$_3$, KF<br>Solvent:<br>xanthone | No melting<br>below 400° C. |
| 7 | 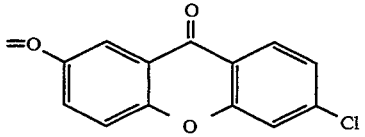 | Example 4<br>Base: Na$_2$CO$_3$, KF<br>Solvent:<br>benzophenone | I.V. = 0.45 |

-continued

Additional polymer examples

| Example | Monomer | Reaction conditions | Polymer properties |
|---------|---------|---------------------|--------------------|

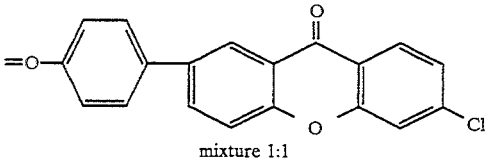

mixture 1:1

What is claimed is:

1. A process for preparing a polymer or copolymer having recurring units of the formula

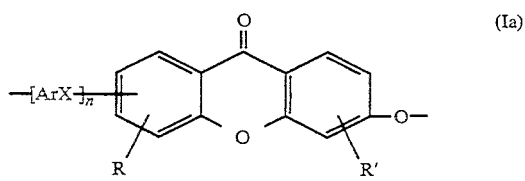

and/or

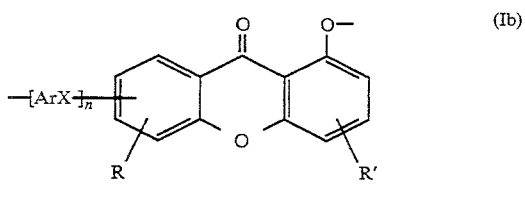

or both, where
R and R', which are the same or different, are hydrogen, alkyl, alkoxy, aryl, aryloxy groups or benzofused radicals,
Ar is a divalent aromatic radical,
X is a direct bond, —O— or —S—, and
n is zero or one, comprising:
nucleophilically polycondensing at a temperature from 200° to 400° C., under essentially anhydrous conditions in the presence or absence of a polar, aprotic aromatic solvent, at least one hydroxyhalogen-substituted xanthone of the formula IIa or IIb

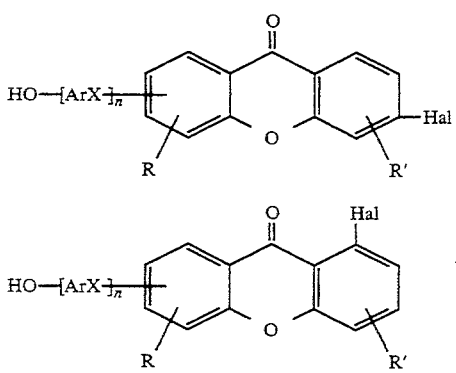

where
R, R', Ar, X and n are as defined above, and
Hal is selected from the group consisting of fluorine and chlorine.

2. A process for preparing a polymer or copolymer having recurring units of the formula Ia and/or Ib of claim 1, comprising:
nucleophilically polycondensing, under essentially anhydrous conditions in the presence or absence of a polar, aprotic aromatic solvent, at least one hydroxyhalogen-substituted benzophenone compound of the formula IIIa or IIIb

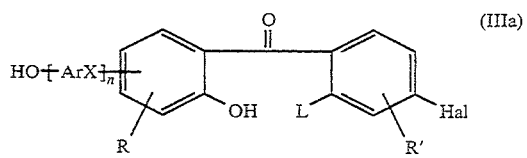

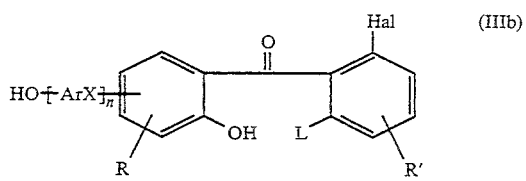

where R, R', Ar, X, and n are as defined in claim 1, Hal is selected from the group consisting of fluorine and chlorine, and
L is a fugic group that can be displaced by intramolecular nucleophilic substitution.

3. The process as claimed in claim 1, wherein the polycondensing is carried out with at least one said hydroxyhalogen of the formula IIa or IIb together with at least one hydroxyhalogen compound of the formula IV HO—Ar'—Hal     (IV)

where
Ar' is a divalent aromatic radical having 12 to 26 carbon atoms that contains at least one keto or sulfonyl group that is in the ortho-position or para-position to the Hal group, and Hal is selected from the group consisting of a chlorine and fluorine group that is situated in the outermost aromatic nucleus.

4. The process as claimed in claim 1, wherein the polycondensing is carried out in the presence of a carbonate or bicarbonate of sodium or potassium or a mixture thereof.

5. The process as claimed in claim 2, wherein the polycondensing is carried out with at least one said hydroxyhalogen of the formula IIIa or IIIb together with at least one hydroxyhalogen compound of the formula IV HO—Ar'—Hal     (IV)

where
Ar' is a divalent aromatic radical having 12 to 26 carbon atoms that contains at least one keto or sulfonyl group that is in the ortho-position or para-position to the Hal group, and Hal is selected from the group consisting of a chlorine and fluorine group that is situated in the outermost aromatic nucleus.

6. The process as claimed in claim 12, wherein L is a chlorine or fluorine group.

7. The process as claimed in claim 2, wherein the polycondensing is carried out in the presence of a carbonate or bicarbonate of sodium or potassium or a mixture thereof.

8. The process as claimed in claim 1, wherein the polycondensing is carried out at a temperature from 200° to 350° C.

9. The process as claimed in claim 1, wherein the polycondensing is carried out in a first step at 200° C. and in a second step at 320° C.

10. The process as claimed in claim 1, wherein the polycondensing is carried out at a temperature from 320° to 350° C.

11. A process for preparing a polymer or copolymer having recurring units of the formula

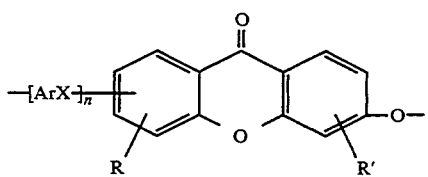

and/or

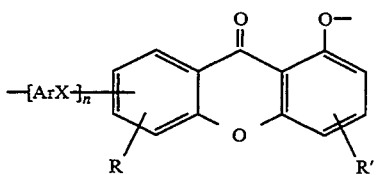

or both, where
R and R', which are the same or different, are hydrogen, alkyl, alkoxy, aryl, aryloxy groups or benzofused radicals,
Ar is a divalent aromatic radical,
X is a direct bond, —O— or —S—, and
n is zero or one, consisting essentially of:
nucleophilically polycondensing at a temperature from 200° to 400° C., under essentially anhydrous conditions in the presence or absence of a polar, aprotic aromatic solvent, at least one hydroxyhalogen-substituted xanthone of the formula IIa or IIb

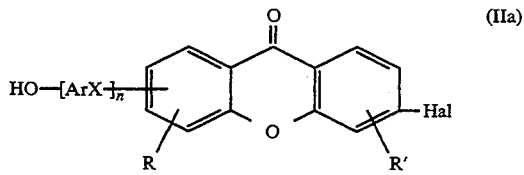

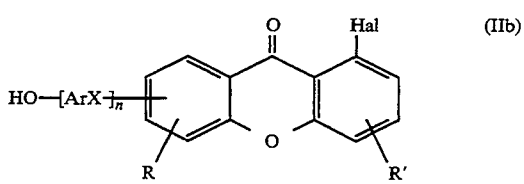

where
R, R', Ar, X and n are as defined above, and
Hal is selected from the group consisting of fluorine and chlorine.

12. The process as claimed in claim 1, wherein the polycondensation is carried out in an inert gas atmosphere.

13. The process as claimed in claim 12, wherein said inert gas atmosphere is a nitrogen or argon atmosphere.

14. The process as claimed in claim 13, wherein said inert gas atmosphere is a nitrogen atmosphere.

15. The process as claimed in claim 1, wherein said Hal is a chlorine group, L is a chlorine group, Ar is a phenylene group, R and R' are the same or different and are selected from the group consisting of hydrogen, methyl, phenyl, methoxy and phenoxy.

16. The process as claimed in claim 7, wherein said Hal is a chlorine group, L is a chlorine group, Ar is a phenylene group, R and R' are the same or different and are selected from the group consisting of hydrogen, methyl, phenyl, methoxy and phenoxy.

17. The process as claimed in claim 15, wherein said R and R' are hydrogen.

18. The process as claimed in claim 16, wherein said R and R' are hydrogen.

* * * * *